United States Patent
Schmutzer et al.

(10) Patent No.: US 10,758,161 B2
(45) Date of Patent: Sep. 1, 2020

(54) PATIENT MOBILITY ASSESSMENT DEVICE

(71) Applicant: Firefly Medical, Inc., Fort Collins, CO (US)

(72) Inventors: Stephen E. Schmutzer, Laporte, CO (US); Darrell Schoenig, Bellvue, CO (US)

(73) Assignee: Firefly Medical, Inc., Fort Collins, CO (US)

( * ) Notice: Subject to any disclaimer, the term of this patent is extended or adjusted under 35 U.S.C. 154(b) by 201 days.

(21) Appl. No.: 15/558,976

(22) PCT Filed: Mar. 16, 2016

(86) PCT No.: PCT/US2016/022670
§ 371 (c)(1),
(2) Date: Sep. 15, 2017

(87) PCT Pub. No.: WO2016/160344
PCT Pub. Date: Oct. 6, 2016

(65) Prior Publication Data
US 2018/0242888 A1    Aug. 30, 2018

Related U.S. Application Data

(60) Provisional application No. 62/139,496, filed on Mar. 27, 2015.

(51) Int. Cl.
*A61B 5/11*    (2006.01)
*A61B 50/13*    (2016.01)
(Continued)

(52) U.S. Cl.
CPC .............. *A61B 5/1113* (2013.01); *A45B 3/00* (2013.01); *A61B 5/1112* (2013.01);
(Continued)

(58) Field of Classification Search
CPC .............. A61H 2201/5007; A61H 3/04; A61H 2201/5012; A61H 2201/5043;
(Continued)

(56) References Cited

U.S. PATENT DOCUMENTS

| 907,171 A | 12/1908 | Poles et al. |
| D45,770 S | 5/1914 | Shaw |

(Continued)

FOREIGN PATENT DOCUMENTS

| JP | S49062892 | 6/1974 |
| JP | H01284250 | 11/1989 |

(Continued)

OTHER PUBLICATIONS

Blickman Catalog, Nezzie Ambulation Device. Accessible on the Internet at URL: <http://www.blickman.com/products/0429000000> [Last Accessed Mar. 2, 2015].

(Continued)

*Primary Examiner* — Christine H Matthews
*Assistant Examiner* — Joshua Daryl D Lannu
(74) *Attorney, Agent, or Firm* — Leydig, Voit & Mayer, Ltd.

(57) ABSTRACT

Provided herein are patient mobility assessment devices having a mobility assistance device with an incorporated distance tracker for use in assessing the ambulation of a recovering medical patient. The distance tracker can be integrated into or removably attached to the mobility assistance device. The information obtained may be displayed on the mobility assistance device and/or at a nurse's station or other remote location for convenient monitoring of patient ambulation. Also provided herein are methods for evaluating patient ambulation using the mobility assessment device and (Continued)

optionally, provision of therapeutic ambulation protocols to a display on the device to assist with patient physical therapy and recovery.

42 Claims, 8 Drawing Sheets

(51) Int. Cl.
    *A61M 5/14*     (2006.01)
    *A61B 5/00*     (2006.01)
    *A61H 3/04*     (2006.01)
    *G01C 22/00*     (2006.01)
    *G01S 19/14*     (2010.01)
    *G16H 40/67*     (2018.01)
    *A45B 3/00*     (2006.01)
    *G06F 19/00*     (2018.01)
    *A45B 9/00*     (2006.01)

(52) U.S. Cl.
    CPC .......... *A61B 5/1118* (2013.01); *A61B 5/6812* (2013.01); *A61B 5/7445* (2013.01); *A61B 50/13* (2016.02); *A61H 3/04* (2013.01); *A61M 5/1415* (2013.01); *G01C 22/00* (2013.01); *G01S 19/14* (2013.01); *G06F 19/3418* (2013.01); *G06F 19/3481* (2013.01); *G16H 40/67* (2018.01); *A45B 2009/002* (2013.01); *A61B 5/1115* (2013.01); *A61B 5/6894* (2013.01); *A61H 2201/5007* (2013.01); *A61H 2201/5012* (2013.01); *A61H 2201/5043* (2013.01); *A61H 2201/5048* (2013.01); *A61H 2201/5064* (2013.01); *A61H 2201/5097* (2013.01); *A61H 2203/0406* (2013.01)

(58) Field of Classification Search
    CPC .... A61H 2201/5048; A61H 2201/5064; A61H 2201/5097; A61H 2203/0406; G01C 22/00; A61M 5/1415; A61B 5/7445; A61B 5/6894; A61B 5/1115; A61B 5/1118; A61B 5/6812; A61B 5/1112; A61B 50/13; A61B 5/1113; G16H 40/67; G01S 19/14; G06F 19/3418; G06F 19/3481; A45B 3/00; A45B 2009/002
See application file for complete search history.

(56) References Cited

U.S. PATENT DOCUMENTS

| | | | |
|---|---|---|---|
| 1,612,148 A | 12/1926 | Oettinger |
| 2,583,114 A | 1/1952 | Monteith |
| 2,596,055 A | 5/1952 | Thomas |
| 2,794,612 A | 6/1957 | Clifton |
| 2,795,387 A | 6/1957 | Elsey |
| 3,437,296 A | 4/1969 | Hinz |
| 3,533,583 A | 10/1970 | Azim |
| 3,719,789 A | 3/1973 | Harnden, Jr. |
| 4,251,044 A | 2/1981 | Olson |
| 4,266,765 A | 5/1981 | Sandoval |
| 4,332,378 A | 6/1982 | Pryor |
| 4,341,381 A | 7/1982 | Norberg |
| 4,541,596 A | 9/1985 | Price |
| D281,453 S | 11/1985 | Digianfilippo et al. |
| 4,725,027 A | 2/1988 | Bekanich |
| 4,744,536 A | 5/1988 | Bancalari |
| D298,460 S | 11/1988 | Pryor |
| 4,807,837 A | 2/1989 | Gawlik et al. |
| 4,832,294 A | 5/1989 | Eidem |
| 4,867,273 A | 9/1989 | Schaevitz |
| 4,892,279 A | 1/1990 | Lafferty et al. |
| 4,905,944 A | 3/1990 | Jost et al. |
| 4,907,794 A | 3/1990 | Rose |
| D310,570 S | 9/1990 | Wells |
| 5,167,389 A | 12/1992 | Reimers |
| 5,411,044 A | 5/1995 | Andolfi |
| 5,458,305 A | 10/1995 | Woodward |
| 5,479,953 A | 1/1996 | Pasulka |
| 5,526,894 A | 6/1996 | Wang |
| 5,556,065 A | 9/1996 | Wadley |
| 5,617,958 A | 4/1997 | Laug et al. |
| 5,622,344 A | 4/1997 | Gracie |
| D385,348 S | 10/1997 | Ward et al. |
| 5,704,577 A | 1/1998 | Gordon |
| D390,953 S | 2/1998 | Ward et al. |
| 5,772,162 A | 6/1998 | Lin |
| 6,056,249 A | 5/2000 | Filion |
| D434,495 S | 11/2000 | Whalen |
| 6,161,850 A | 12/2000 | James et al. |
| D436,167 S | 1/2001 | Ebert |
| 6,209,829 B1 | 4/2001 | Yu |
| 6,226,833 B1 | 5/2001 | Kawaguchi et al. |
| 6,296,260 B1 | 10/2001 | Schiavone |
| 6,296,263 B1 | 10/2001 | Schultz et al. |
| D457,239 S | 5/2002 | Kunik |
| 6,430,761 B1 | 8/2002 | Brandorff et al. |
| 6,467,797 B1 | 10/2002 | Lofy et al. |
| D479,164 S | 9/2003 | Wu |
| 6,619,599 B2 | 9/2003 | Elliot et al. |
| 6,698,789 B2 | 3/2004 | Reimers et al. |
| 6,839,939 B2 | 1/2005 | Donakowski |
| D503,909 S | 4/2005 | Tolfsen et al. |
| 6,899,660 B1 | 5/2005 | Chin et al. |
| 6,969,031 B2 | 11/2005 | Ugent et al. |
| 6,980,111 B2 | 12/2005 | Nolte |
| 6,983,915 B2 | 1/2006 | Adelman |
| D519,423 S | 4/2006 | Tolfsen |
| 7,041,941 B2 | 5/2006 | Faries et al. |
| 7,048,222 B1 | 5/2006 | Curtiss |
| 7,065,812 B2 | 6/2006 | Newkirk et al. |
| 7,118,079 B2 | 10/2006 | Kung |
| 7,278,615 B2 | 10/2007 | Schubert et al. |
| 7,281,691 B2 | 10/2007 | Adelman |
| 7,353,731 B2 | 4/2008 | Lin |
| D568,467 S | 5/2008 | Cottone |
| 7,591,479 B2 | 9/2009 | Golias |
| 7,607,243 B2 | 10/2009 | Berner, Jr. et al. |
| 7,634,824 B2 | 12/2009 | Gramkow et al. |
| 7,726,327 B2 | 6/2010 | Battiston |
| D622,377 S | 8/2010 | Jackson |
| D627,063 S | 11/2010 | West et al. |
| D628,691 S | 12/2010 | Sung et al. |
| D630,731 S | 1/2011 | Schmutzer et al. |
| 7,935,030 B1 | 5/2011 | Nesbitt |
| 8,136,773 B2 | 3/2012 | Schmutzer et al. |
| 8,292,310 B2 | 10/2012 | Turner |
| 8,403,275 B2 | 3/2013 | Cote |
| 8,534,616 B2 | 9/2013 | Schmutzer et al. |
| 8,662,458 B2 | 3/2014 | Henault et al. |
| 8,756,993 B2 | 6/2014 | Lamy-Perbal et al. |
| 9,173,803 B2 | 11/2015 | Schmutzer et al. |
| D791,937 S | 7/2017 | Schoenig et al. |
| 2003/0178538 A1 | 9/2003 | Hasloecher et al. |
| 2005/0139736 A1 | 6/2005 | Breda et al. |
| 2005/0230573 A1 | 10/2005 | Ligertwood |
| 2006/0001226 A1 | 1/2006 | Refsum |
| 2007/0000325 A1 | 1/2007 | Weber et al. |
| 2007/0267551 A1 | 11/2007 | Townsend |
| 2008/0156946 A1 | 7/2008 | Schmutzer et al. |
| 2008/0176720 A1 | 7/2008 | Vanmanshoven |
| 2008/0210831 A1 | 9/2008 | Considine |
| 2008/0221928 A1 | 9/2008 | Garcia et al. |
| 2009/0242006 A1* | 10/2009 | Warren ................ A61H 3/00 135/66 |
| 2010/0318005 A1 | 12/2010 | Amonetie |
| 2011/0016628 A1 | 1/2011 | Masterson |
| 2011/0023920 A1* | 2/2011 | Bolton ................ A61H 3/04 135/66 |
| 2011/0030749 A1 | 2/2011 | Miller |
| 2011/0290979 A1 | 12/2011 | Henault et al. |
| 2012/0035427 A1 | 2/2012 | Friedman et al. |
| 2012/0133111 A1 | 5/2012 | Schmutzer et al. |

(56) References Cited

U.S. PATENT DOCUMENTS

| | | | |
|---|---|---|---|
| 2012/0290217 A1 | 11/2012 | Shoval et al. | |
| 2013/0261964 A1* | 10/2013 | Goldman | G01C 21/12 701/500 |
| 2013/0270799 A1 | 10/2013 | Schmutzer et al. | |
| 2014/0237721 A1 | 8/2014 | Lemire | |
| 2014/0367540 A1 | 12/2014 | Gaal et al. | |
| 2016/0157951 A1 | 6/2016 | Schoenig et al. | |

FOREIGN PATENT DOCUMENTS

| | | | |
|---|---|---|---|
| JP | H03046338 | | 4/1991 |
| JP | 3040162 | | 8/1997 |
| JP | 2002211405 | | 7/2002 |
| JP | 2005506244 | | 3/2005 |
| JP | 2006335355 | | 12/2006 |
| WO | WO 2004101034 | | 11/2004 |
| WO | WO 2008085698 | | 7/2008 |
| WO | WO 2015010060 | | 1/2015 |
| WO | WO-2015010060 A1 * | 1/2015 | ............. A61B 50/13 |

OTHER PUBLICATIONS

European Search Report with Written Opinion corresponding to European Patent Application No. 2007869691, dated Feb. 9, 2015.

Extended European Search Report corresponding to European Patent Application No. 14826018.5, dated Feb. 7, 2017.

International Search Report with Written Opinion corresponding to International Patent Application No. PCT/US2007/088433, dated Aug. 7, 2008.

International Search Report with Written Opinion corresponding to International Patent Application No. PCT/US2014/047254, dated Nov. 12, 2014.

International Search Report with Written Opinion corresponding to International Patent Application No. PCT/US2016/022670, dated Jul. 26, 2016.

LivenGood PACE. Accessible on the Internet at URL: <http://www.livengoodmed.com> [Last Accessed Mar. 10, 2015].

Non-Final Rejection with Response corresponding to U.S. Appl. No. 11/961,834, dated May 12, 2011.

Office Action corresponding to Australian Patent Application No. 2007342126, dated Jul. 25, 2012.

Office Action corresponding to Chinese Patent Application No. 2014800519191, dated Dec. 27, 2016.

Office Action corresponding to Japanese Patent Application No. P2009-544881, dated Aug. 6, 2013.

Office Action corresponding to Japanese Patent Application No. P2009-544881, dated Jul. 3, 2012.

Office Action in corresponding Japanese Patent Application No. P2013-252977, dated Oct. 14, 2014.

\* cited by examiner

PATIENT MOBILITY ASSESSMENT DEVICE

CROSS-REFERENCE TO RELATED APPLICATIONS

This application is a U.S. National Stage Application under 35 U.S.C. § 371 of International Application No. PCT/US2016/022670, filed Mar. 16, 2016, which claims the benefit of and priority to U.S. Provisional Patent Application No. 62/139,496 filed Mar. 27, 2015, each of which is hereby incorporated by reference in its entirety to the extent not inconsistent herewith.

BACKGROUND OF INVENTION

Provided are ambulation devices and related methods that include distance tracking features for assessing the mobility of recovering medical patients. Early and safe ambulation is critical to patient recovery, and methods to encourage, measure and assess patient ambulation are an important aspect with respect to evolving healthcare protocols. A convenient means of measuring patient mobility, such as by the distance, speed, and regularity with which a patient is able to walk after having a medical procedure is desired.

U.S. Pub. No. 2008/0221928 describes a system for monitoring the activity of a medical patient. That system employs a device worn by the patient that communicates with specially located receivers when the patient is nearby. Similarly, U.S. Pub. No. 2012/0035427 discloses a device for telemetrically monitoring a patient. However, those devices are not built into or attached to a mobility assistance device, and they do not directly measure distance traveled. Furthermore, systems that must be worn by the patient are susceptible to misuse and/or being misplaced so that the reliability of any patient mobility assessment is called into question.

U.S. Pub. No. 2012/0290217 describes a global positioning system (GPS) device that is worn by a subject outside of a hospital setting for monitoring daily activity and physical condition, including distance walked. However, that device is not built into or attached to a mobility assistance device used by a patient undergoing rehabilitation in a medical setting.

U.S. Pat. Nos. 7,041,941, 6,980,111, and U.S. Pat. Pub. No. 2014/0367540 similarly describes devices and methods for locating medical items. However, those systems do not measure the distance traveled of the equipment or patients using them.

There is a need in the art for a mobility assistance apparatus that can be used to directly measure and track the ambulation of a recovering patient in a hospital or medical recovery setting in a safe, reliable and automated manner that is unobtrusive to the goal of patient ambulation.

SUMMARY OF THE INVENTION

Provided herein are devices and related methods useful for assessing patient mobility and ambulation in a manner that is non-obtrusive and integrated with typical patient routine in a medical facility. In particular, provided is a distance tracker configured for connection with a mobility assistance device, such as a device that provides patient support in a medical facility, including for patients connected to one or more of IV fluids, pumps, monitors, or other medical devices. The distance tracker may be part of an independent component that is retro-fitted to a mobility assistance device. Alternatively, the distance tracker may be integrated within the mobility assistance device to provide a complete package system. The unique configuration and combination of a patient mobility device and distance tracker is referred herein as a "patient mobility assessment device" to reflect the ability of the devices and related methods to both assist with ambulation while providing a convenient and reliable mechanism to assess and assist patient recovery by the amount and type of ambulation by the patient.

Early and safe ambulation is critical to patient recovery, and if done correctly, it can abbreviate the duration of a patient's hospital stay. Some hospitals are now marketing themselves with a "mobility emphasis", as they know this is an important development in healthcare. Methods to encourage and measure patient ambulation are few, which is why there is a need in the art for the distance tracking feature provided by any of the patient mobility assessment devices described herein. Advantages of the methods and devices described herein include the ability to reliably and efficiently track and monitor one or multiple patients in a manner that is convenient, including from the perspective of each of the patient and a medical caregiver charged with assessing patient recovery, including patient ambulation. This is an important aspect as part of the recovery process may be intimately tied with safe and reliable early post-operative or post-procedure ambulation, with increased ambulation assisting with recovery, including shorter hospital stays and recovery periods.

The patient mobility assessment device may comprise a mobility assistance device and a distance tracker connected to the mobility assistance device. The distance tracker may comprise a sensor integrated or otherwise connected to the mobility assistance device for tracking a distance traveled by the mobility assistance device. A display or any other type of read-out type device is operably connected to the sensor and configured to display a patient mobility parameter, including the distance traveled by the mobility assistance device. "Distance traveled" is used broadly herein to refer to the actual distance a device moves or a parameter calculated or related thereto, such as speed, time taken to travel the distance, or number of ambulatory trips taken. The display may be connected to any surface of the mobility assistance device, including a surface that is convenient for the patient to observe during ambulation and/or for a caregiver to observe during patient ambulation. The display may be reversibly or more permanently incorporated into the mobility device, such as flush to a surface, so that the display is not readily or accidentally removed.

The display may be configured to electronically display from the sensor a patient mobility parameter. The patient mobility parameter may be distance traveled over a time period, total distance traveled by a patient, total movement time, travel speed, number of ambulatory trips taken, or a combination thereof. The display may be further configured to indicate a date and time for the distance traveled, and/or a distance traveled over X period of time. The display may be connected wirelessly to the sensor or may be hard-wired to the sensor. The display may alternatively, or in addition to, be positioned at a distance from the mobility assistance device and configured for remote assessment of distance traveled by the mobility assistance device. The display may functionally have two separate display portions, with one positioned at a distance and the other local to the mobility device, for assessment at both the mobility assistance device and assessment remote from the mobility assistance device, such as at a central caregiver station where multiple mobility devices may be tracked.

The display may further comprise a receiving unit configured to receive distance traveled information from the sensor. The display may be a mobile device configured to also function as a sensor, a controller, a receiver, or a combination thereof. The display may be a digital display having a small form factor that displays distance traveled in response to a signal from the sensor. The display may be a liquid crystal display. The display may further comprise a controller to control the display or information stored in the receiving unit, wherein the controller comprises one or more buttons, and wherein the buttons are flush-mounted with respect to a surface of the display or controller. The buttons may provide a means to reset the display at, for example, the start of a new shift, a new day, a new time period, or a new excursion event. Similarly, the display may be used to input information, such as a unique patient identifier, so that a single patient mobility assessment device may be used to track multiple different patients, including in situations where there are more patients than mobility assessment devices available. The receiving unit may be configured to be reset by a code so that the patient cannot inadvertently reset the device. The relevant information for each unique patient identifier may be electronically stored at a remote distance, such as at a caregiver's workstation.

The readout on the display or information on the central processing unit (cpu) can be reset or otherwise manipulated and read by a medical caregiver at various scheduled points, such as at the beginning and end of a shift. This can provide additional data or information regarding a patient's recovery over different specified time periods and permits a caregiver to further tailor, prescribe and evaluate mobility protocols.

The sensor may comprise a caster configured to connect to the mobility assistance device, the caster comprising a wheel, a magnet connected to the wheel, a fork, wherein the sensor is connected to the fork and the wheel is rotatably connected to the fork, wherein the sensor is configured to detect each rotation of the wheel by the passage of the magnet past the sensor, and wherein the sensor comprises a relay configured to send a signal indicating a distance traveled to a display of a receiving unit. The caster may be removably connected to the mobility assistance device. As caster wheels can be readily connected to the mobility assistance device, pulled out and/or replaced, such a sensor configuration is readily used as an accessory attachment, including for the retrofitting of a pre-existing mobility assistance device, thereby cost-effectively and efficiently upgrading the device. Other add-on components are readily incorporated, including software and hardware upgrades to medical computer workstations for electronic communication with upgraded mobility assistance devices.

The sensor may be positioned within an interior portion of the mobility assistance device. The sensor may be incorporated within a GPS device. The GPS device may have an integrated display. The sensor may be a physical-type sensor, such as a pedometer or accelerometer type sensor. Accordingly, the devices provided herein are compatible with a range of different types of sensors, including those that physically measure as for a physical-type sensor, or electronically measure for a GPS or other "tracking-by-location" sensor that measures the distance a patient walks and relays that information to the receiving unit, whether the receiving unit is on the mobility assistance device itself, or at another location.

The sensor may be incorporated within a mobile device, such as a mobile phone, a tablet, or a handheld device, that is connected to the mobility assistance device. The mobile device may be configured to also function as a display, a controller, a receiver, or any combination thereof.

The distance tracker may be a built-in feature of a mobility assistance device. Alternatively, the distance tracker may be an add-on accessory to the mobility assistance device, and may be provided separately from a mobility assistance device. The distance tracker may be removably connected to the mobility assistance device or may be more permanently affixed, connected, or embedded within a mobility assistance device. For instance, the distance tracker may be affixed within a hollow portion of the device, such as an inner-facing surface of a wall, including of a mast, base leg or mobility handle. The distance tracker may be powered by a battery. Accordingly, for embodiments where the tracker is affixed within an internal portion of the unit, an access compartment may be provided to facilitate battery or tracker replacement. The access compartment may be discrete and reliably secured, thereby minimizing risk of theft, tampering or otherwise damage to the tracker.

The mobility assistance device may comprise an accessory connector for connecting to or receiving the display and/or receiving unit of the distance tracker. The accessory connector may comprise a magnet, an adhesive, a fastener, a touch fastener such as Velcro, or a snap-fit attachment. Alternatively the accessory connector may comprise an orifice on the mobility assistance device for securely receiving an appendage on the display, including a rubber appendage.

The methods and devices provided herein facilitate measurement or calculation of one or more patient mobility parameters. Examples of patient mobility parameters of interest include distance traveled, total movement time, trip or ambulation frequency, travel speed, or a combination thereof. The patient mobility assessment device may be configured to receive and display a patient mobility protocol from a medical caregiver or provider based on a desired patient mobility parameter, which, in turn, may depend on patient recovery and ambulation. The patient mobility protocol may be total movement time, total movement distance, average speed range, ambulation frequency or a combination thereof. This protocol may vary with time post-procedure, such as for increasing time since a procedure, an increase in the amount, intensity and/or frequency of ambulation. In other words, the patient mobility parameter may be time-varying, reflecting a desired ambulation time and intensity that increases with time since the medical procedure. In this manner, a patient during ambulation phase with the device herein may readily understand the day's goals and work to achieve the goal in a safe and reliable manner. Both patient and medical personal may readily assess progress. For example, the first day with the ambulation may correspond to a relatively low ambulation frequency of one or two times, with a low duration of at least 5 minutes and low total distance travelled for each ambulation event of at least 20 meters. On subsequent days or time periods, the frequency, duration and intensity may be increased. Any timeframe as desired may be utilized, such as dividing the day into morning, afternoon and evening, as desired, for tracking these individual time periods.

The distance tracker may be configured to automatically disengage after a no-input time period and automatically engage upon receipt of a sensor input so that the distance tracker is disengaged or in a sleep mode when the mobility assistance device is not moving for a no-input time period, such as a time period of at least three seconds, or 10 seconds or more. This can save battery charge, while accommodating brief pauses.

The patient mobility assessment device may further comprise a receiving unit operably connected to the sensor and configured to store the distance traveled information provided by the sensor, wherein the receiving unit is configured to receive distance traveled information from the sensor, and wherein the sensor is configured to uniquely communicate with the receiving unit. The patient mobility device may further comprise a central processor unit within a display housing of the display for storing the distance traveled information provided by the sensor.

The receiving unit and/or display may be positioned at a nurses' station, or located with a medical caregiver for centralized evaluation. At this location, there may be a rack or section where a series of receiving units or displays are mounted for convenient evaluation of several patients, wherein each receiving unit or display is configured to uniquely communicate with a different and specific sensor. The receiving unit may be operably connected to a printer for printing a hard-copy or paper record of the data for placement in a patient's chart. Of course, this rack may be a virtual rack, wherein a graphical user interface on a computer-connected display provides a graphical or visual representation of one or more of the patient mobility parameters, and related status of the mobility assessment device. From such a station, protocols may be readily developed and input so as to display on a display positioned on the mobility assistance device observable by the patient and/or medical caregiver with the patient. In situations where it is desired that the patient ambulate at-will without pressure of tracking ambulation progress, the display may be removed from the mobility assessment while having the information regarding ambulation safely provided to a receiving station, including for electronic tracking at a workstation.

In an aspect, the mobility assistance device of the patient mobility assessment device corresponds to any of the devices disclosed in U.S. Pat. Nos. 8,136,773, 8,534,616, 9,173,803, 8,662,458, PCT Pub. No. WO 2015/010060 (published Jan. 22, 2015) and U.S. application Ser. No. 29/517,155 (filed Feb. 10, 2015), having a distance tracker connected thereto. For example, the mobility assistance device may comprise a mast having a top end, a bottom end and an outer surface extending between the top and bottom ends; a base comprising a first base leg and a second base leg to form a two-sided base footprint, wherein one end of each of the first and second base legs connect to the mast to form a vertex region, and the mast and two-sided base footprint form a mast angle, wherein the mast angle is an acute angle so that at least a portion of the mast extends within a region that vertically extends from the two-sided base footprint; a pole connected to the mast for securing a medical component, wherein the pole has a longitudinal axis that is separated from the mast outer surface by a separation distance; a mobility handle connected to said mast or said base; a first wheel connected to the first base leg; a second wheel connected to the second base leg; a third wheel connected to the vertex region, wherein each of the wheels are configured to stably contact a support surface on which the device rests and the mobility handle is configured to receive an applied force to stably ambulate the device over the support surface. The display portion may be connected to any convenient surface of the device. Convenient refers to the ability for the display to be viewed during ambulation. Accordingly, convenient surfaces include the mast, the pole, the handles, or a platform or ledge from which the mobility handles extend.

The mobility assistance device may comprise a mast; a first base leg connected to the mast; a second base leg connected to the mast; wherein the first and second base legs form a two-sided base footprint; an oxygen tank holder comprising: an upper tank holder connected to the mast for coupling with an upper portion of an oxygen tank; and a lower tank holder connected to the first or the second base leg for coupling with a base portion of an oxygen tank.

Also provided herein is a distance tracker that is configured to connect to a mobility assistance device. The distance tracker may comprise a caster having a fork with a top fork surface, a bottom fork surface and a wheel connection component, wherein a mobility assistance device connection element is connected to the fork top surface for attaching the caster to the mobility assistance device, a wheel rotatably connected to the wheel connection component, a magnet connected to the wheel, a sensor connected to the fork. The sensor can then detect each rotation of the wheel by detecting the passage of the magnet. Magnets may be positioned on the caster of the mobility assistance device to trigger the sensor every time the caster revolves or the magnets pass by the sensor. The sensor is prompted to alert the receiving unit each time the caster revolves. This represents distance traveled according to πD, where D is the wheel diameter, and thereby, the figures on the display graduate as the mobility assistance device travels with patient ambulation, reflecting increased travel distance with ambulation time. As caster wheels are readily pulled out and replaced, such a caster configuration is readily configured as an accessory attachment to retrofit a mobility assistance device. Similarly, damaged sensors may be readily replaced.

The distance tracker may further comprise a receiving unit operably connected to the sensor, wherein the sensor further comprises a sending unit for sending distance traveled information to the receiving unit. The distance tracker may further comprise a display operably connected to the sensor, wherein the display is configured to display distance traveled information from the sensor. The distance tracker wheel connection component may be a pin or other similar protrusion configured to connect with or insert into an orifice on a mobility assistance device base portion, such as a terminal portion of a base leg.

Also provided are methods of evaluating patient ambulation comprising monitoring a signal generated by a sensor from any of the patient mobility assessment devices described herein, and determining a patient mobility parameter, including over a certain period of time. The patient mobility parameter may be one or more of total distance traveled, duration of travel, average speed, and longest continuous travel time.

Also provided are methods of monitoring the signal from the sensor, including local monitoring of a display connected to the mobility assistance device, or remote monitoring of a display or receiving unit at a position distant from the mobility assistance device. The monitoring may be either real-time during patient ambulation and/or at a time period after patient ambulation is complete. The method may further comprise actively programming the mobility assessment device with a patient therapy protocol. For example, a physical therapist or other medical caregiver may input a target goal of one or more of total ambulation time, total ambulation distance, average ambulation speed, or similar ambulatory parameter as desired. When the goal is attained, an alert may be sent to the display mounted on the mobility assistance device, so that a patient or medical caregiver with the patient is alerted that the goal has been achieved. This goal may correspond to a daily goal, a time period goal, such as broken into increments, such as ranging between 1 hour and 8 hours, or an excursion goal. The inputting of the target goal may occur remotely, such as at a workstation that is remote from the mobility assistance device. Alternatively, the inputting may occur at the display/controller unit connected to the mobility assistance device, such as prior to patient ambulation as the medical caregiver prepares the patient and deploys the mobility assistance device. In this manner, control limits are provided to avoid risk of patient overexertion while also reliably quantifying ambulation.

Without wishing to be bound by any particular theory, there may be discussion herein of beliefs or understandings of underlying principles relating to the devices and methods disclosed herein. It is recognized that regardless of the ultimate correctness of any mechanistic explanation or hypothesis, an embodiment of the invention can nonetheless be operative and useful.

DETAILED DESCRIPTION OF THE INVENTION

Figure 1A:
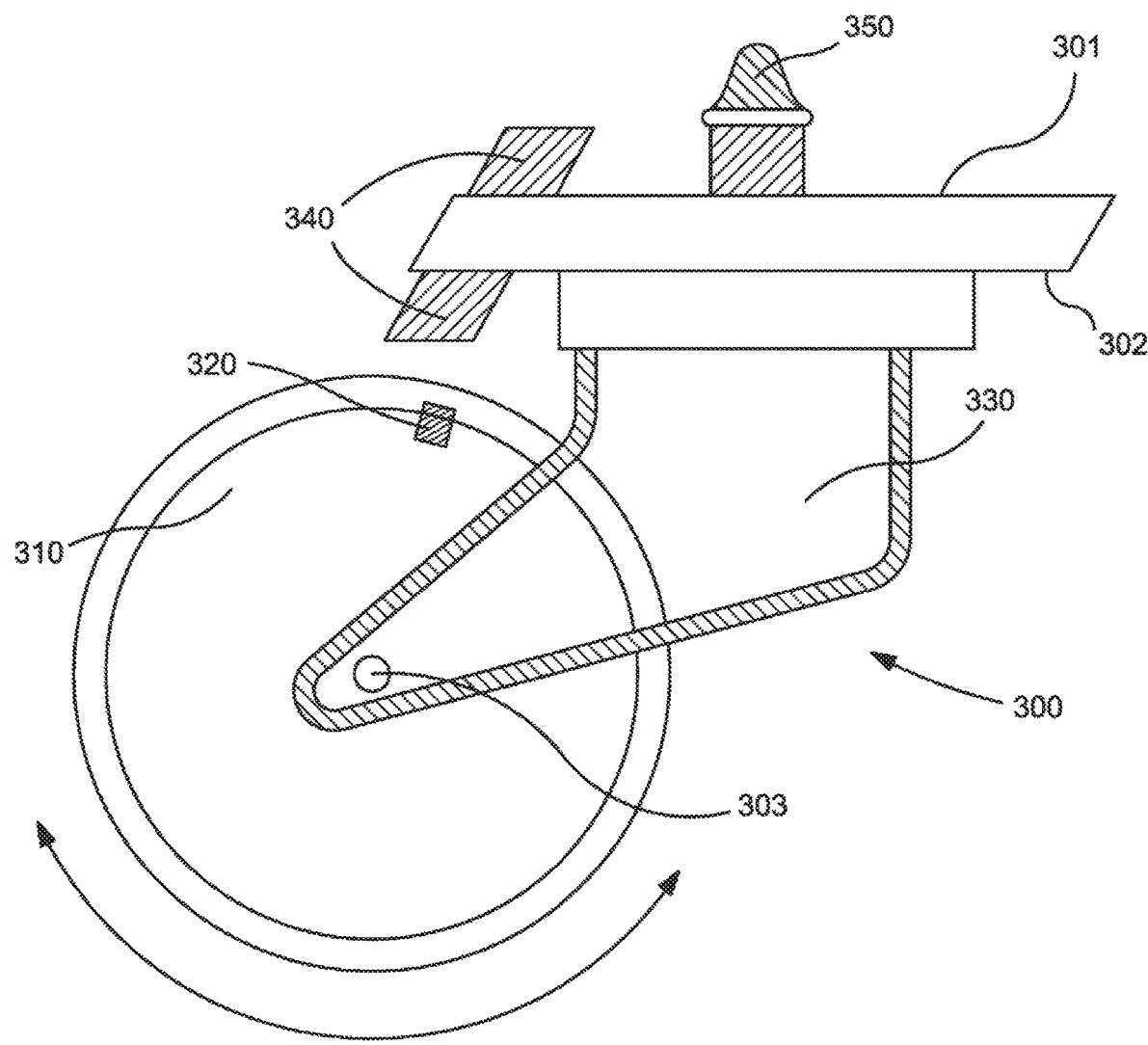
FIG. 1A. Wheel caster with a distance tracker for distance tracking based on wheel rotation.

In general, the terms and phrases used herein have their art-recognized meaning, which can be found by reference to standard texts, journal references and contexts known to those skilled in the art. The following definitions are provided to clarify their specific use in the context of the invention.

The term "mobility assistance device" refers to a mobile intravenous (IV) pole or a device for aiding in patient ambulation. Examples include, but are not limited to, any of those described in U.S. Pat. Nos. 8,136,773, 8,534,616, 9,173,803, 8,662,458, PCT Pub. No. WO 2015/010060 (published Jan. 22, 2015) and U.S. application Ser. No. 29/517,155 (filed Feb. 10, 2015), each of which are specifically incorporated by reference herein.

A "distance tracker" is a device that measures the distance that a patient has traveled. Examples include a GPS, a pedometer, a fitness monitor, a smartphone, mini-computer with display connected to a magnetic-based sensor or GPS-based sensor (either wired or wirelessly), or other activity tracker. The invention is compatible with a wide range of distance trackers with very different means for tracking distance. For example, the tracking means may be purely electronic, without mechanically moving parts, such as GPS devices or wireless tracking devices, including via applications within a smart-phone or other wireless devices, such as a fitness tracker. Alternatively, the device may be more mechanical in nature, such as a sensing unit that detects passage of a sensing element, wherein each passage of a sensing element corresponds to a known distance. This may be via a magnet and sensor, wherein one of the sensor or magnet is connected to a wheel such that for each passage of the magnet detected by the sensor, the distance traveled is $\pi D$, where D is the diameter of the wheel. With a distance tracker, other parameters of interest, including patient mobility parameters, may be determined.

As used herein, the term "sensor" refers to the technical aspect of the distance tracker that measures distance traveled and sends the information to the display or receiver via wireless communication or hard-wire communication.

"Patient mobility parameter" refers to one or more variables useful in characterizing patient ambulation or mobility. Examples include, but are not limited to, distance traveled, total movement time, travel speed, ambulation frequency (e.g., the number of distinct trips over a time period), and corresponding individual parameters for each trip with, as desired, an average thereof, or any combination thereof. In an aspect, travel speed incorporates the concept of calculating average speed only during actual movement, such that the clock stops counting when the patient stops to rest, and resumes when the patient begins walking. For example, this can be implemented by an "auto-on-off" feature in the distance tracker, such as in the display or receiving unit. The receiver clock stops if it receives no input from the sensor for a no-input time period, for example at least 3 seconds. Of course, the invention is compatible with any number of seconds, depending on the application of interest and associated patient characteristics. Accordingly, the distance tracker re-starts the clock as soon as it begins receiving input again upon mobility assistance device motion. This specific application is useful for calculating average speed associated with actual movement of the mobility assistance device. So if a patient is ambulating for 15 minutes total, but they stopped and chatted with another patient for 5 of those minutes, their average speed would be based on the 10 minutes they were actually moving. Similarly, the patient mobility parameter may also provide indication of patient endurance, such as the ability to continuously move over an uninterrupted time period with an average ambulation velocity greater than a caregiver-selected ambulation velocity.

As used herein, an "accessory connector" refers the component(s) that securely connect the receiving unit and/or display to the mobility assistance device. Examples include, but are not limited to, an orifice in the mobility assistance device that receives an appendage configured into the receiving unit/display; an adhesive attachment; a magnetic attachment; a snap-fit attachment; a strap with connection means, such as Velcro; a fastener; or a platform for resting the receiving unit/display on.

A "mobile device," as used herein, refers to a device that is capable of displaying, receiving, controlling, or sensing distance traveled information, or any combinations thereof. Examples include, but are not limited to, a smart phone or a tablet. In this aspect, the phone can act as the receiver and controller rather than only the sensor. This is a recognition that GPS signals may be weak or non-existent in many buildings. Of course, the invention is compatible with any future arising signaling technologies that provide reliable coverage in closed spaces. For those situations in which GPS signaling is not readily available or desired, applications may be incorporated into the handheld device or smart phone to display all the metrics; the handheld device or phone simply connects to the sensor via Bluetooth in a simple, reliable, robust, and cost-effective manner. This avoids the need for a dedicated receiver/controller. Furthermore, a caregiver could monitor the patient via the handheld device or phone, and optionally, the patient could via their handheld device or phone as well. This is a low-cost approach for budget-sensitive applications, such as in a hospital setting.

"Operably connected" refers to a configuration of elements, wherein an action or reaction of one element affects another element, but in a manner that preserves each element's functionality. For example, a display operably connected to the sensor refers to the ability of the display to provide information regarding ambulation without impacting the functionality of the sensor or the mobility assistance device.

Example 1: Mobility Assistance Device with Caster Distance Tracker and Receiving Unit Referring to FIGS. 1-3 the mobility assistance device 100 may have a caster 300 and a display 220. Optionally the display 220 may be incorporated into a receiving unit 240 as shown in FIGS. 2A and 2B.

Figure 1B:
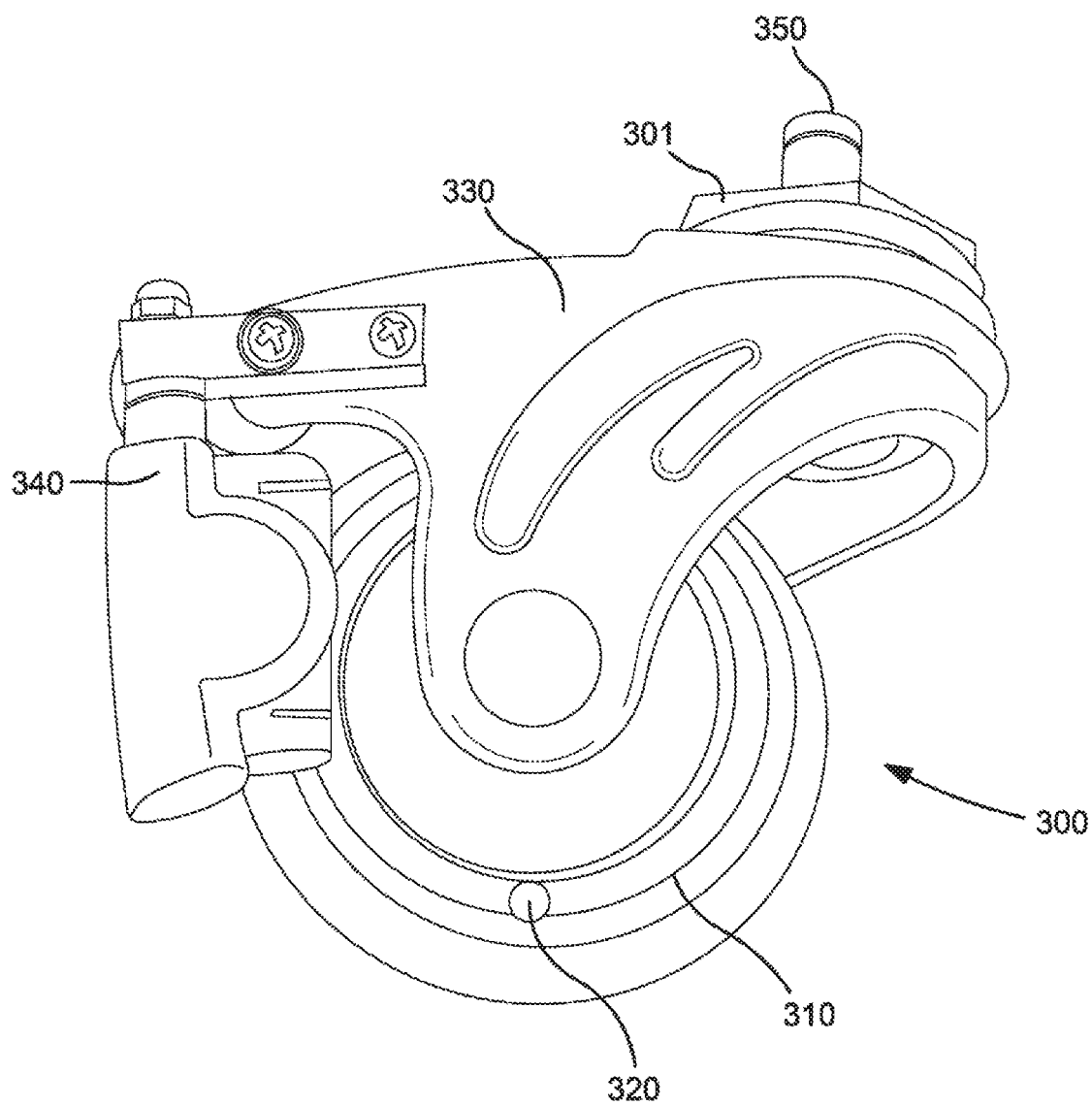
FIG. 1B. Second example of caster accessory unit with a sensor positioned to reliably detect a magnet embedded in wheel, each time the magnet passes the sensor.

As illustrated in FIGS. 1A and 1B, the caster 300 has a wheel 310, a magnet 320, and a fork 330 that is connected to a sensor 340 having a relay. As the wheel 310 rotates in either direction (indicated by the double sided arrow), the magnet 320 passes the sensor 340, which relays a signal indicating distance traveled to a receiving unit 240 (FIGS. 2A and 2B) that may be connected via protrusion 230 to the mobility assistance device 100 via orifice 120. The caster 300 may also have a pin or protrusion 350 for attaching the caster to the mobility assistance device, such as by positioning with a correspondingly configured orifice positioned in the base. The fork may have a top fork surface 301, bottom fork surface 302 and a mobility assistance device connection element, illustrated as protrusion or pin 350 connected to top fork surface 301. The caster may have a wheel connection component 303 to rotatably connect wheel 310 to the fork 330 for reliably sensing of wheel rotation.

Figure 2A:
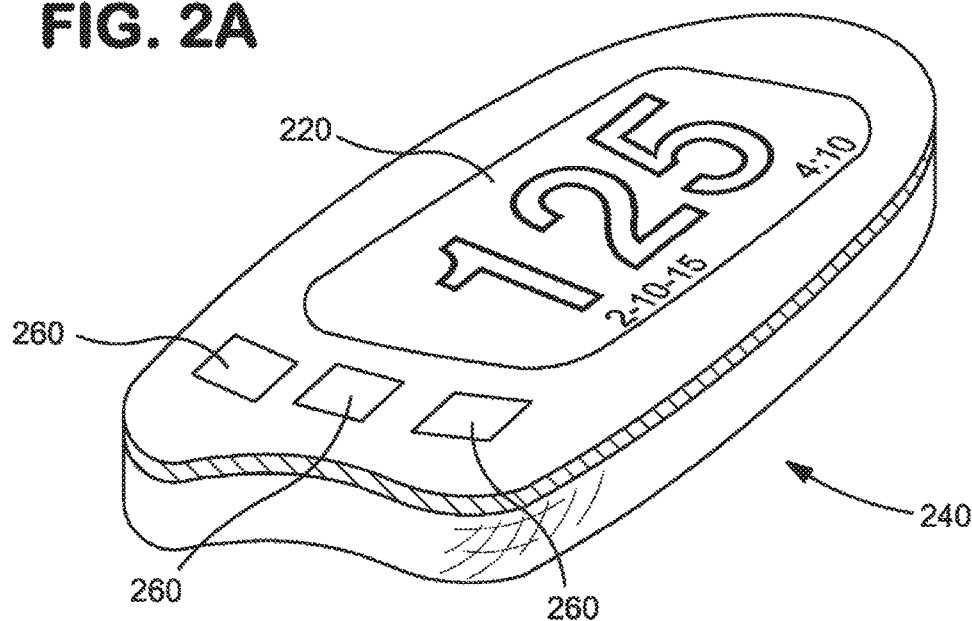
FIG. 2A. Perspective view of a display accessory unit with control buttons.
Figure 2B:
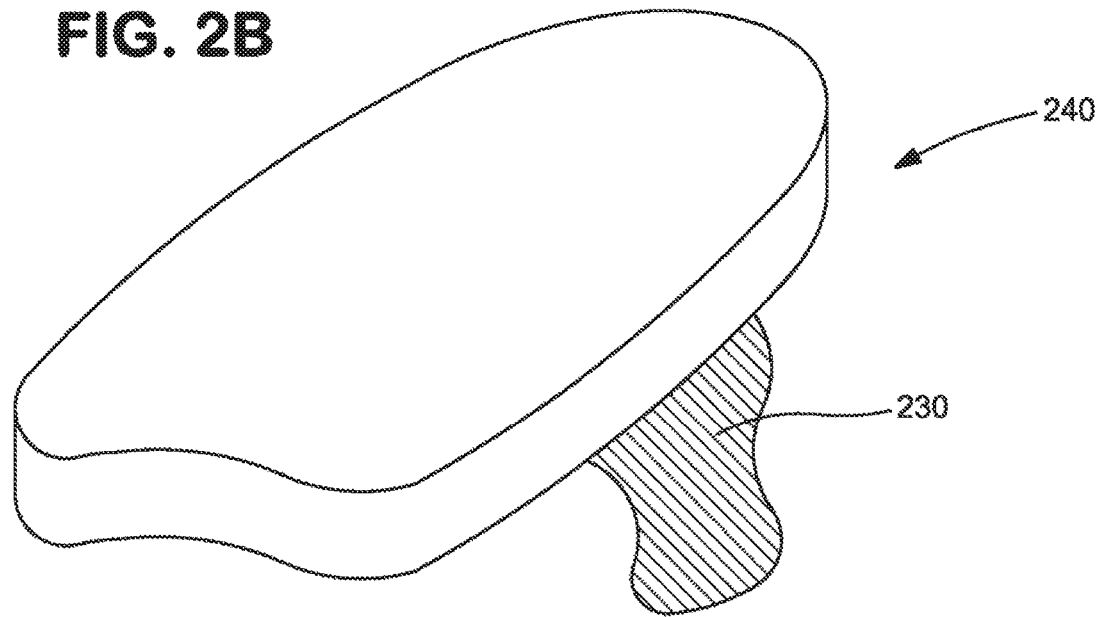
FIG. 2B. View of an appendage for mounting a display unit to a mobility assistance device.

FIGS. 2A and 2B illustrate a display or receiving unit 240. The front of the receiving unit 240, as shown in FIG. 2A may have a display 220 and a controller that includes one or more flush-mounted buttons 260 for controlling the display 220 and/or information stored in the receiving unit 240, including a cpu within the receiving unit 240. The receiving unit may include an appendage 230 configured to insert into an orifice 120 on the mobility assistance device 100, as illustrated in FIG. 3A and FIG. 4.

Figure 3A:
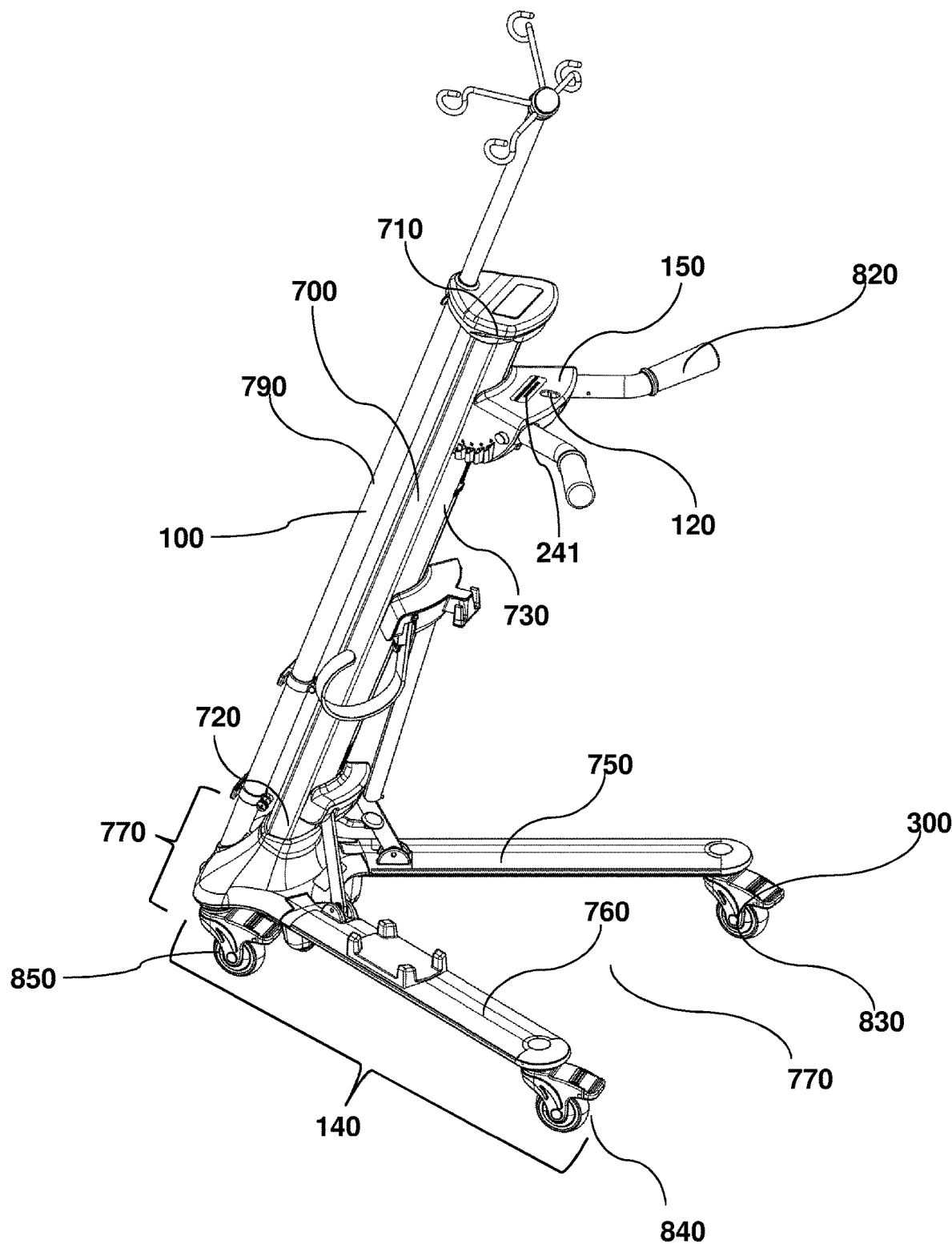
FIG. 3A. Perspective view of a mobility assistance device configured for use with a patient mobility assessment device, including an accessory unit thereof.
Figure 4:
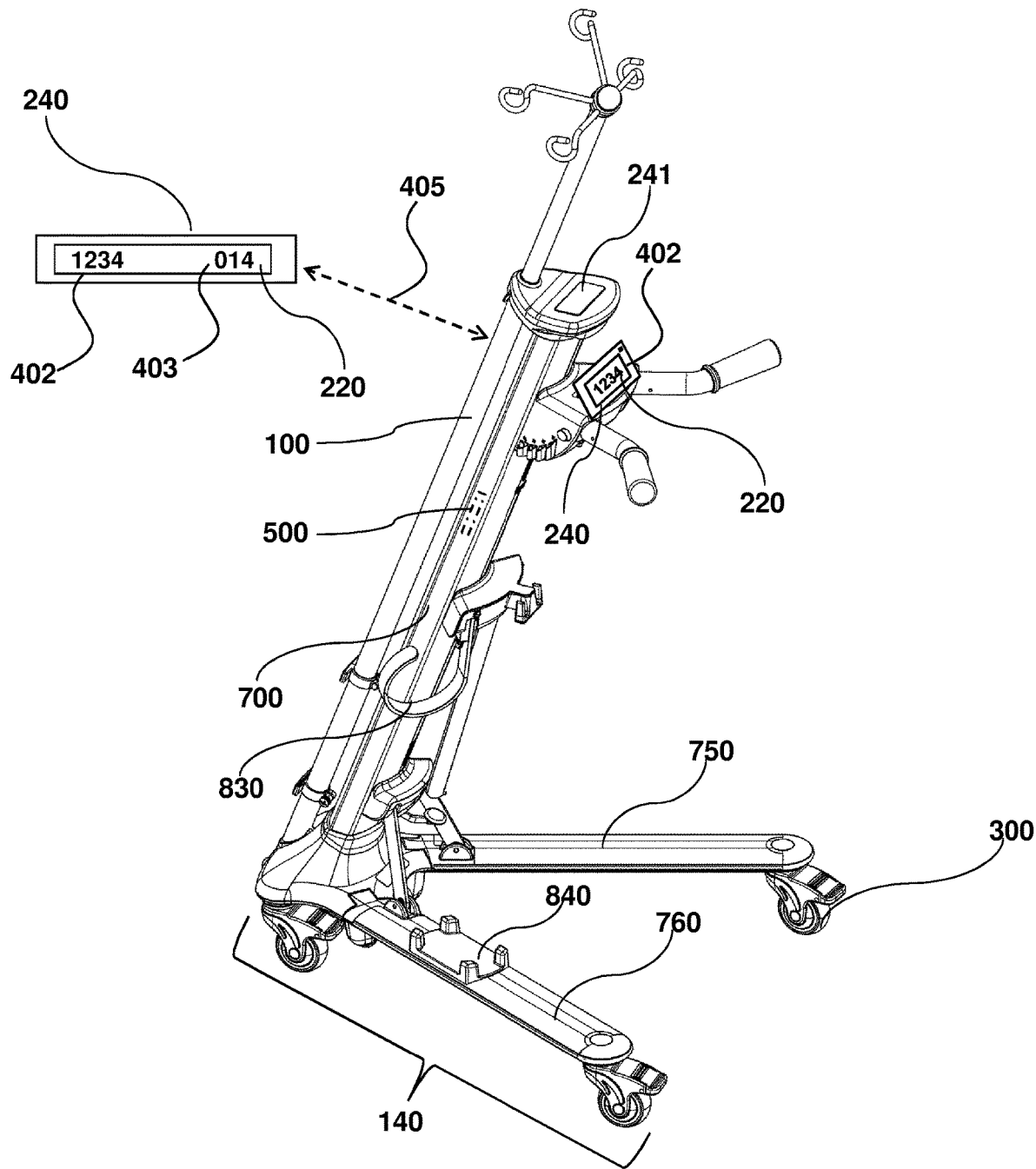
FIG. 4 illustrates a mobility assessment device with a display operably connected thereto. Also illustrated is a receiving unit wirelessly connected to the distance tracker to display a patient mobility parameter and an indication as to which mobility device/patient is associated with the patient mobility parameter, including at a remote location, such as a medical caregiver station.

FIG. 3A illustrates a mobility assistance device 100 with a caster 300 either built in or attached to the base portion 140. The orifice 120 is configured to receive the appendage or protrusion 230 of a display or receiving unit 240. The point of connection, or orifice, is illustrated as at the handle bracket or platform 150. Of course, the connection point may be at any desired location of the mobility assistance device, such as on the mast, handles, base, or any other portion that is of convenience. A convenient point of connection for viewing by a patient or medical caregiver during ambulation is at the mobility handle or a component connected to the mobility handle, as illustrated by a component 150 that is a platform that is, in turn, connected to the mobility handles 820. Similarly, the display may extend from a bracket or other mounting system that is connected to or near the top end of the mast 710. The connection may be rotatable, so that the display faces toward the patient to facilitate patient viewing or around one of the other sides of the mast 710 to facilitate viewing by a person accompanying the ambulating device, such as a medical caregiver.

Example 2: Integrated Systems

Figure 5:
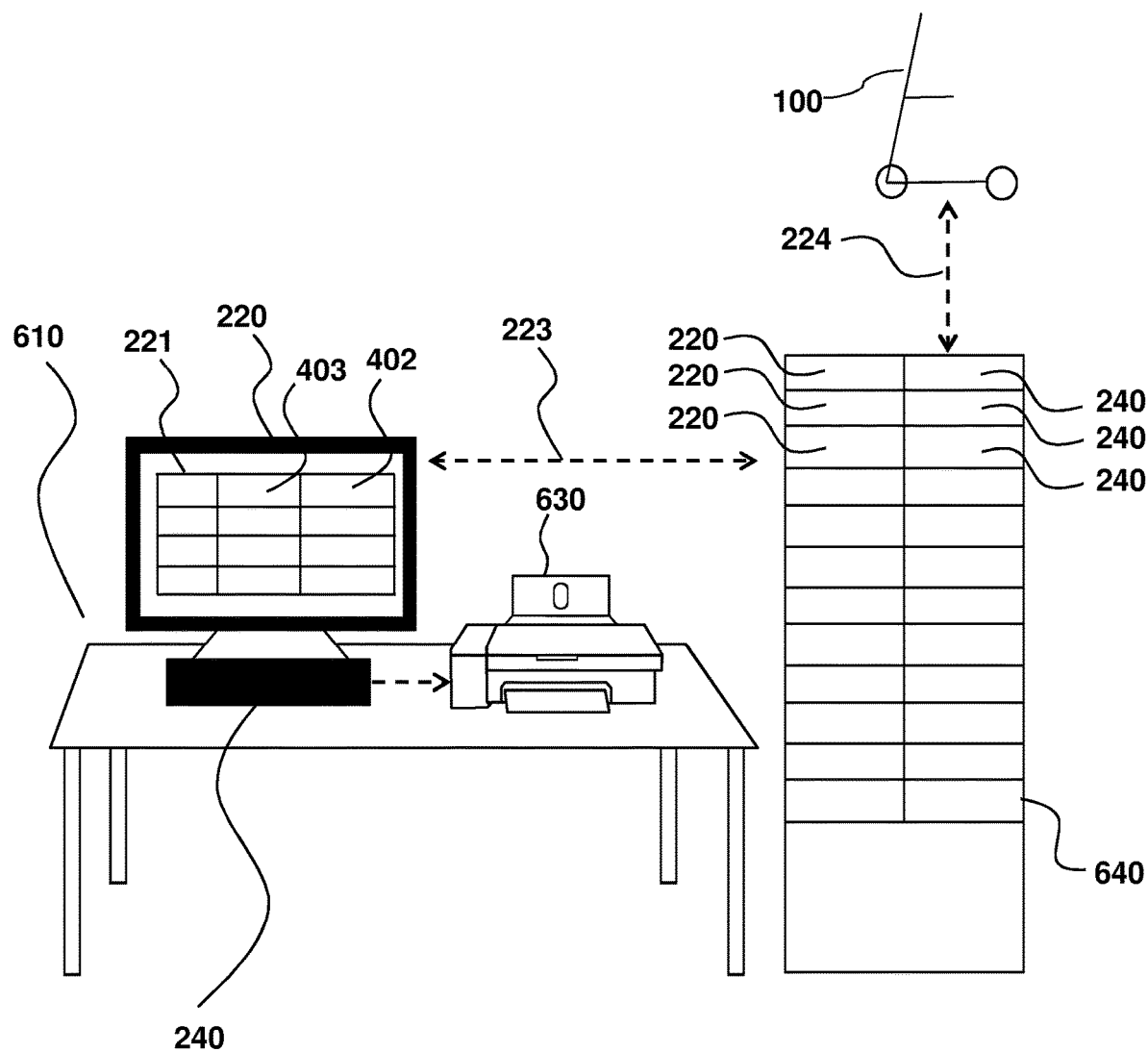
FIG. 5. A workstation, such a nurse's station or medical caregiver station, remote from the mobility assistance device, with a plurality of receiving units and displays for monitoring and control of patient ambulation and protocols. A printer may be employed to print records of patient ambulation and related information.

The tracking system illustrated in FIGS. 1A and 1B is one example of an accessory type feature that can be used to convert a mobility assistance device to a patient mobility assessment device, such as by incorporation of the wheel caster 300 with distance tracker. In other examples, the distance tracker may be a GPS-type location-based tracking device that can be positioned in other locations, besides the wheel. In other words, the distance tracker may be connected at other locations than at a wheel caster. For applications where it is desired that the tracking sensor device is discretely used, the sensor may be located in an interior portion 500 of the mobility assistance device, as illustrated by FIG. 4. Of course, any other convenient location may be used, including any interior-facing or exterior facing surface. One example of another possible location is identified as 241 on FIGS. 3A and 4, including a flush-mounted display. As illustrated in FIG. 4, a display 220 or, more generally, display with receiving unit 240 may be used to assess patient mobility. The receiving unit 240 and/or display 220 may be integrated into the mobility assistance device 100, removably attached to the mobility assistance device 100, or placed at a remote location as indicated by the dashed line 405 between the mobility assistance device 100 and physically separated display 240. One convenient remote location is a nurse's station or other medical caregiver workstation 610, as illustrated by FIG. 5. The receiving unit 240 and/or display 220 may be flush-mounted with the mobility assistance device 100. If the receiving unit 240 is integrated into the mobility assistance device 100, the device may also include an access compartment, for manipulation of the receiving unit 240 such as battery replacement. The display 220 may provide any number of patient mobility parameters 402 such as distance traveled, total movement time, travel speed, number of unique ambulation events, or a combination thereof. The display 220 may also provide a patient and/or mobility assistance device 100 identifier 403, where any information is explicitly tied to specific sensor connected to a specific mobility assistance device and/or a uniquely identified patient.

Figure 3B:
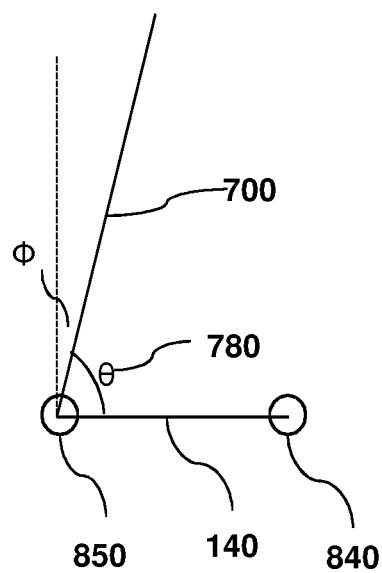
FIG. 3B. Side schematic diagram of a mobility assistant device illustrating the mast angle, $\theta$, formed by the angle between the mast and the base. $\phi$ shows a corresponding angle with respect to vertical.
Figure 3C:
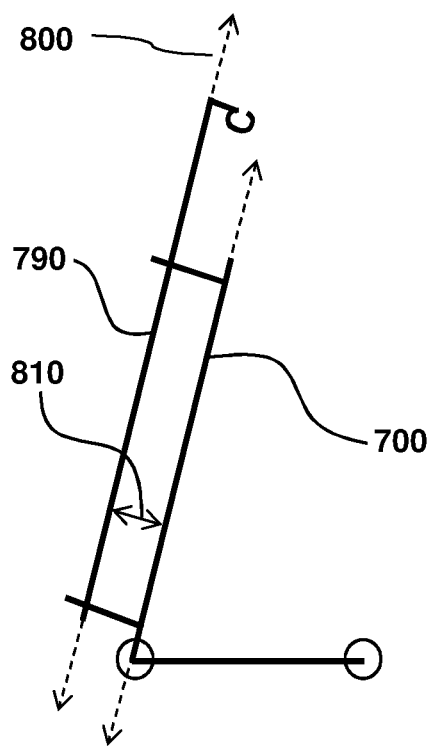
FIG. 3C. Schematic illustration of the mast and pole axis of a mobility assistance device, with the separation distance between the pole and mast outer surface.

Exemplary mobility assistance devices are illustrated in FIGS. 3A-3C, and may include a mast 700 having a top end 710, a bottom end 720 and an outer surface 730 extending between the top and bottom ends; a base 140 comprising a first base leg 750 and a second base leg 760 to form a two-sided base footprint 770, wherein one end of each of the first 750 and second base legs 760 connect to the mast 700 to form a vertex region 770, and the mast 700 and two-sided base footprint 770 form a mast angle 780, a non-zero angle (φ) relative to vertical and an acute angle (θ) relative to the base 140; a pole 790 connected to the mast 700 for securing a medical component, wherein the pole 790 has a longitudinal axis 800 that is separated from the mast outer surface 730 by a separation distance 810; a mobility handle 820 connected to the mast 700 or the base 140; a first wheel 830 connected to the first base leg 750; a second wheel 840 connected to the second base leg 760; a third wheel 850 connected to the vertex region 770, wherein each of the wheels are configured to stably contact a support surface on which the device rests and the mobility handles 820 are configured to receive an applied force to stably ambulate the device over the support surface. The handles may be in a swept-out configuration and have a handle platform 150 that is a convenient point of attachment for a display and/or receiving unit operably connected to the sensor. The sensor may be connected at any number of locations as desired and as dictated by the underlying sensor mechanism. For example, if the sensor is for detection of a magnet that moves with wheel rotation, the sensor may be connected to detect wheel rotation as the magnet passes the sensor. If GPS or equivalent sensing mechanism, the sensor may be positioned in a relatively inaccessible area to avoid sensor loss or destruction, including in an internally located position. An access panel may, of course, be employed to permit sensor servicing or replacement, including a lockable access panel. As desired, the sensor may be wirelessly connected to the receiving unit or display. The devices provided herein are, of course, compatible with other connection types, including a hard-wired connection, particularly, as the wires may run through protected locations, including along interior walls of the mast to meet up with the display and/or receiving unit positioned at a distance from the sensor. Of course, as discussed the sensor itself may be part of the display, thereby avoiding the need for multiple physically distinct components.

Another exemplary mobility assistance device is illustrated in FIG. 4 and may include a mast 700; a first base leg 750 connected to the mast 700; a second base leg 760 connected to the mast 700; wherein the first 750 and second base legs 760 form a two-sided base footprint 770; an oxygen tank holder comprising an upper tank holder 830 connected to the mast 700 for coupling with an upper portion of an oxygen tank, and a lower tank holder 840 connected to the first 750 or the second base leg 760 for coupling with a base portion of an oxygen tank. A display 220 may be conveniently positioned near the handle region, such as on a handle shelf, for convenient viewing by an ambulation patient. Of course, the devices and methods are compatible with a display connected to any other surface, as desired and as convenient for the individual needing to view the display.

Example 3: Patient Mobility Assessment

Referring to FIGS. 4 and 5, a receiving unit 240 may be used to functionally obtain information useful for patient mobility assessment. The receiving unit 240 may provide patient mobility parameters 402, such as total distance traveled, total steps, duration of travel, average speed, and/or longest continuous travel time. These parameters 402 may be monitored on a display 220 that is connected to the mobility assistance device (FIG. 4); or on a display 220 that is located at a remote location, such as at a remote work or nurses' station 610 (FIG. 5). A graphical user interface 221 may be provided on the display 220, via communication connection between the receiving unit 240 and workstation computer 240, as indicated by dashed arrow 223. This allows rapid and efficient evaluation of patient ambulation, even for multiple mobility assessment devices that are moving simultaneously. The receiving unit itself may correspond to a computer that is operably connected to any of the sensors, including directly or indirectly via intermediary components, including intermediary displays and/or receiving units/controllers.

The caregivers' workstation 610 may include a rack 640 that is configured to receive a plurality of receiving units 240 and/or a plurality of displays 220. The receiving units 240 and/or displays 220 may be operably connected to a printer 630 for printing hard-copy records or an electronics record patient file. Equivalent electronic-compatible records may be similarly obtained and electronically saved. Of course, such a physical rack may be replaced with a virtual rack in the form of a GUI 221 displayed on a computer monitor. The parameters 402 may be monitored in real-time during patient ambulation, or at a time after patient ambulation is complete. Additionally, the receiving unit 240 may be configured to also send a patient therapy protocol to a display 220 connected to the mobility assistance device, such as desired distance, time, speed, and the like, and countdown thereof, for a patient using the mobility assistance device and a medical caregiver supervising the patient, as indicated by dashed arrow 224 between receiving units 240 and mobility assistance device 100. Such interaction between patient use and medical caregiver supervision facilitates improved patient outcome related to safe and well-characterized ambulation. This interaction is also indicated by a double-ended arrow 405 on FIG. 4.

Figure 6:
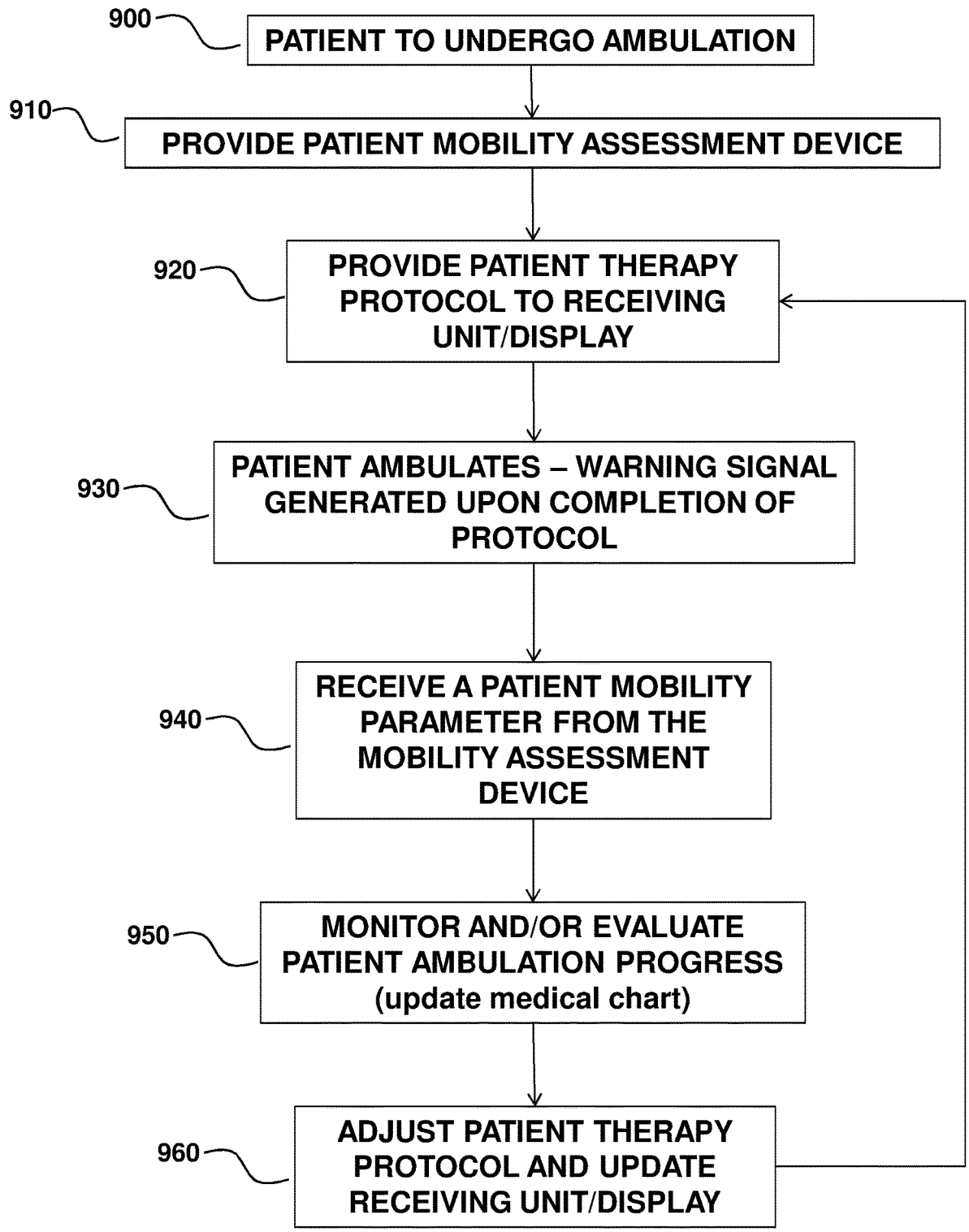
FIG. 6 is a flow chart summary for use of the patient mobility assessment device to provide a patient therapy protocol for a patient desiring to ambulate with any of the patient mobility assessment devices described herein.

FIG. 6 is a flow-chart summary of a method for evaluating patient ambulation and/or providing a patient ambulation therapy protocol for efficient physical therapy tailored to each patient, including for a floor, unit or clinic having multiple patients with multiple devices, including using any of the devices and components discussed in FIGS. 1-5. Any patient desiring to ambulate, including patients having undergone a medical procedure or who are recovering, may benefit from the methods and devices provided herein, as indicated by step 900. A patient mobility assessment device is provided to the patient, and the device uniquely tagged to the specific patient (910). The method and devices, of course, are also compatible with non-medical procedures, such as individuals in short or long-term care, and persons requiring assistance in ambulating where an individual at a distance, such as family, friends, or caregiver, desires an assessment as to how often the person is ambulating with the device. Accordingly, the term "patient" is used broadly, including in the context of FIG. 6, and may include any individual ambulating with an assistance device.

A patient therapy protocol may be provided to the patient, such as to the receiving unit or display, as summarized at step 920. In this manner, the patient may see the goals and strive to achieve them in a safe and reliable setting. Any number of protocols may be provided, with one or more goals of ambulation time, number of trips, distances, speed and combinations thereof, including for individual trips and/or cumulative trips. For initial use, the protocol may be blank, leaving the patient free to provide their own goals. Alternatively, there may be a preset initial goal, including a preset initial goal that depends on one or more patient characteristics and/or medical procedure(s).

To avoid overexertion, optionally a warning or "target met" signal is generated when goal(s) are met (930). Irrespective of whether a target is met, the devices provided herein ensure a patient mobility parameter may be seamlessly received from the mobility assessment device, as indicated at 940. The received step may simply be a caregiver who receives information directly from a display connected to the mobility assessment device. Alternatively, the received step may be via transmission to a remote work station, including any of the stations illustrated in FIGS. 4-5, for inclusion into a patient chart or electronic record at step 950. Accordingly, at a medical caregiver's convenience, the patient therapy protocol may be updated and provided to the mobility assessment device for subsequent use by the patient via step 960. The feedback step between step 960 and 920 indicates that patient therapy protocol may depend, at least in part, on the patient mobility parameter determined from the patient mobility assessment device. In this manner, the physical movement therapy may be tailored to each individual patient, instead of a more simple one-size-fits all ambulation protocol. In addition, any of the methods provided herein are equally compatible with any number of ambulation patients and mobility assistance devices. For example, the method may be employed at a workstation that can simultaneously track and provide mobility assessment for a plurality of patients, including patients using a plurality of mobility assistance devices. This is schematically illustrated by graphical user interface 221 on display 220 at a work station 610 in FIG. 5. This provides functional benefit of increased medical caregiver efficiency, as evaluation and additional therapy can be provided at one central location, and the devices themselves need not be tracked down and individually observed to obtain the desired information.

STATEMENTS REGARDING INCORPORATION BY REFERENCE AND VARIATIONS

All references throughout this application, for example patent documents including issued or granted patents or equivalents; patent application publications; and non-patent literature documents or other source material; are hereby incorporated by reference herein in their entireties, as though individually incorporated by reference, to the extent each reference is at least partially not inconsistent with the disclosure in this application (for example, a reference that is partially inconsistent is incorporated by reference except for the partially inconsistent portion of the reference).

The terms and expressions which have been employed herein are used as terms of description and not of limitation, and there is no intention in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments, exemplary embodiments and optional features, modification and variation of the concepts herein disclosed may be resorted to by those skilled in the art, and that such modifications and variations are considered to be within the scope of this invention as defined by the appended claims. The specific embodiments provided herein are examples of useful embodiments of the present invention and it will be apparent to one skilled in the art that the present invention may be carried out using a large number of variations of the devices, device components, methods steps set forth in the present description. As will be obvious to one of skill in the art, methods and devices useful for the present methods can include a large number of optional composition and processing elements and steps.

Whenever a range is given in the specification, for example, a temperature range, a time range, a size range, or a composition or concentration range, all intermediate ranges and subranges, as well as all individual values included in the ranges given are intended to be included in the disclosure. It will be understood that any subranges or individual values in a range or subrange that are included in the description herein can be excluded from the claims herein.

All patents and publications mentioned in the specification are indicative of the levels of skill of those skilled in the art to which the invention pertains. References cited herein are incorporated by reference herein in their entirety to indicate the state of the art as of their publication or filing date and it is intended that this information can be employed herein, if needed, to exclude specific embodiments that are in the prior art. For example, when composition of matter are claimed, it should be understood that compounds known and available in the art prior to Applicant's invention, including compounds for which an enabling disclosure is provided in the references cited herein, are not intended to be included in the composition of matter claims herein.

As used herein, "comprising" is synonymous with "including," "containing," or "characterized by," and is inclusive or open-ended and does not exclude additional, unrecited elements or method steps. As used herein, "consisting of" excludes any element, step, or ingredient not specified in the claim element. As used herein, "consisting essentially of" does not exclude materials or steps that do not materially affect the basic and novel characteristics of the claim. In each instance herein any of the terms "comprising", "consisting essentially of" and "consisting of" may be replaced with either of the other two terms. The invention illustratively described herein suitably may be practiced in the absence of any element or elements, limitation or limitations which is not specifically disclosed herein.

One of ordinary skill in the art will appreciate that starting materials, biological materials, reagents, synthetic methods, purification methods, analytical methods, assay methods, and biological methods other than those specifically exemplified can be employed in the practice of the invention without resort to undue experimentation. All art-known functional equivalents, of any such materials and methods are intended to be included in this invention. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

We claim:

1. A patient mobility assessment device comprising:
   a mobility assistance device; and
   a distance tracker connected to the mobility assistance device, wherein the distance tracker comprises:
   a sensor integrated or connected to the mobility assistance device for tracking a distance traveled by the mobility assistance device; and a display operably connected to the sensor and configured to display a patient mobility parameter, or the distance traveled by the mobility assistance device;
wherein the mobility assistance device comprises:
a mast having a top end, a bottom end and an outer surface extending between the top and bottom ends;
a base comprising a first base leg and a second base leg to form a two-sided base footprint, wherein one end of each of the first and second base legs connect to the mast to form a vertex region, and the mast and two-sided base footprint form a mast angle, wherein the mast angle is an acute angle so that at least a portion of the mast extends within a region that vertically extends from the two-sided base footprint;
a pole connected to the mast for securing a medical component, wherein the pole has a longitudinal axis that is separated from the mast outer surface by a separation distance;
a mobility handle connected to said mast or said base;
a first wheel connected to said first base leg;
a second wheel connected to said second base leg; and
a third wheel connected to said vertex region, wherein each of the wheels are configured to stably contact a support surface on which the device rests and the mobility handle is configured to receive an applied force to stably ambulate the device over the support surface.

2. The patient mobility assessment device of claim 1, wherein the display is connected to the mobility assistance device.

3. The patient mobility assessment device of claim 1, wherein the display is wirelessly connected to the sensor.

4. The patient mobility assessment device of claim 3, wherein the display is positioned at a distance from the mobility assistance device and configured for remote assessment of distance traveled by the mobility assistance device.

5. The patient mobility assessment device of claim 1, wherein said distance tracker is stably integrated with the mobility assistance device.

6. The patient mobility assessment device of claim 5, wherein the sensor is positioned within an interior portion of the mobility assistance device.

7. The patient mobility assessment device of claim 1, wherein the display is connected to a surface of the mobility assistance device and configured to electronically display from the sensor the patient mobility parameter.

8. The patient mobility assessment device of claim 7, wherein the patient mobility parameter is selected from the group consisting of: distance traveled, total movement time, travel speed, and a combination thereof.

9. The patient mobility assessment device of claim 8, wherein the distance tracker is configured to automatically disengage after a no-input time period and automatically engage upon receipt of a sensor input so that the distance tracker is disengaged when the mobility assistance device is not moving for a no-input time period and the no-input time period is at least three seconds.

10. The patient mobility assessment device of claim 1, wherein the display is configured to receive and display a patient mobility protocol from a medical caregiver.

11. The patient mobility assessment device of claim 10, wherein the patient mobility protocol is at least partly based on the patient mobility parameter measured by the patient mobility assessment device, and the patient mobility protocol is selected from the group consisting of: total movement time; total movement distance; average speed range; frequency of ambulation; and a combination thereof.

12. The patient mobility assessment device of claim 1, wherein the distance tracker is an add-on accessory to the mobility assistance device.

13. The patient mobility assessment device of claim 12, wherein the distance tracker is removably connected to the mobility assistance device.

14. The patient mobility assessment device of claim 13, wherein the mobility assistance device comprises an accessory connector for receiving the display.

15. The patient mobility assessment device of claim 14, wherein the accessory connector comprises: a magnet, an adhesive, a fastener, a touch fastener, an orifice for receiving a protrusion extending from the display; or a snap-fit attachment.

16. The patient mobility assessment device of claim 14, wherein the accessory connector comprises an orifice and the display further comprises an appendage configured to securely insert into said orifice.

17. The patient mobility assessment device of claim 1, wherein the sensor comprises:
a caster configured to connect to the mobility assistance device, the caster comprising:
a wheel,
a magnet connected to the wheel, and
a fork, wherein the sensor is connected to the fork and the wheel is rotatably connected to the fork, wherein the sensor is configured to detect each rotation of the wheel by the passage of the magnet past the sensor;
wherein the sensor comprises a relay configured to send a signal indicating a distance traveled to a display of a receiving unit.

18. The mobility assistance device of claim 17, wherein the caster is removably connected to the mobility assistance device.

19. The patient mobility assessment device of claim 1, wherein the display further comprises a receiving unit configured to receive distance traveled information from the sensor.

20. The patient mobility assessment device of claim 19, wherein the display is a mobile device configured to also function as a sensor, a controller, a receiver, or any combination thereof.

21. The patient mobility assessment device of claim 19, wherein the display is a digital display having a small form factor configured to connect to the mobility assistance device and to display distance traveled in response to a signal from the sensor.

22. The patient mobility assessment device of claim 21, wherein the display is configured to indicate a date and a time for the distance traveled.

23. The patient mobility assessment device of claim 22, wherein the display further comprises a controller to control the display or information stored in the receiving unit, wherein the controller comprises one or more buttons, and wherein the one or more buttons are flush-mounted with respect to a surface of the controller.

24. The patient mobility assessment device of claim 1, further comprising:
a receiving unit operably connected to the sensor and configured to store distance traveled information provided by the sensor, wherein the receiving unit is configured to receive the distance traveled information from the sensor; wherein the sensor is configured to uniquely communicate with the receiving unit.

25. The patient mobility assessment device of claim 24, further comprising:

a central processor unit for storing the distance traveled information provided by the sensor, wherein the central processor unit is located within a display housing of the display.

26. The patient mobility assessment device of claim 24, wherein the receiving unit or display is positioned at a medical caregiver station.

27. The patient mobility assessment device of claim 26, further comprising a rack configured to receive a plurality of receiving units or a plurality of displays for multiple patient evaluation of mobility at a single location, wherein each receiving unit or display is configured to uniquely communicate with a specific sensor.

28. The patient mobility assessment device of claim 27, wherein the receiving unit is operably connected to a printer for printing a paper hard-copy record for submission to a patient chart, or an electronic equivalent thereof.

29. The patient mobility assessment device of claim 1, wherein the display is a liquid crystal display.

30. The patient mobility assessment device of claim 1, wherein the distance tracker is powered by a battery.

31. The patient mobility assessment device of claim 1, wherein the sensor is incorporated within a GPS device.

32. The patient mobility assessment device of claim 31, wherein the GPS device has an integrated display.

33. The patient mobility assessment device of claim 1, wherein the sensor is incorporated within a mobile device that is connected to the mobility assistance device.

34. The patient mobility assessment device of claim 33, wherein the mobile device is configured to also function as a display, a controller, a receiver, or any combination thereof.

35. The patient mobility assessment device of claim 34, wherein the mobile device is a mobile phone, a tablet, or a handheld device.

36. The patient mobility assessment device of claim 1, wherein the display is connected to:
the mobility handle; or
a component connected to the mobility handle,
wherein the display is oriented in a direction for viewing during ambulation.

37. The patient mobility assessment device of claim 1, wherein the mobility assistance device further comprises:
an oxygen tank holder comprising:
an upper tank holder connected to the mast for coupling with an upper portion of an oxygen tank; and
a lower tank holder connected to the first or the second base leg for coupling with a base portion of the oxygen tank.

38. A method of evaluating patient ambulation comprising:
monitoring a signal generated by the sensor from a plurality of patient mobility assessment devices of claim 1;
determining the patient mobility parameter over a certain period of time, and
providing to the display a patient therapy protocol;
thereby evaluating patient ambulation.

39. The method of claim 38, wherein the patient mobility parameter is one or more of: total distance traveled, duration of travel, average speed and longest continuous travel time.

40. The method of claim 38, wherein the monitoring comprises:
local monitoring of the display connected to the mobility assistance device; or
remote monitoring of the display or receiving unit at a position distant from the mobility assistance device.

41. The method of claim 40, wherein the monitoring of the signal step is real-time during patient ambulation or is at a time period after patient ambulation is complete.

42. The method of claim 40, further comprising simultaneous monitoring of the plurality of mobility assessment devices by remote monitoring with a plurality of displays at a medical caregiver station remotely located from the plurality of mobility assessment devices.

* * * * *